(12) United States Patent
Sonderegger

(10) Patent No.: US 6,796,652 B1
(45) Date of Patent: Sep. 28, 2004

(54) GLARE-PROTECTION DEVICE WITH A SCREENED EVALUATION CIRCUIT

(75) Inventor: Rico Sonderegger, Lengwil (CH)

(73) Assignee: Optrel AG, Wattwil (CH)

( * ) Notice: Subject to any disclaimer, the term of this patent is extended or adjusted under 35 U.S.C. 154(b) by 149 days.

(21) Appl. No.: 10/088,977

(22) PCT Filed: Sep. 15, 2000

(86) PCT No.: PCT/CH00/00497

§ 371 (c)(1),
(2), (4) Date: Mar. 26, 2002

(87) PCT Pub. No.: WO01/22906

PCT Pub. Date: Apr. 5, 2001

(30) Foreign Application Priority Data

Sep. 29, 1999 (CH) .............................................. 1793/99

(51) Int. Cl.[7] .......................... G02C 7/10; G02F 1/1335
(52) U.S. Cl. .......................... 351/44; 2/905; 250/201.1; 349/14; 359/609
(58) Field of Search .............................. 351/44; 349/13, 349/14, 16; 250/200, 201.1; 2/905, 906; 359/601, 609

(56) References Cited

U.S. PATENT DOCUMENTS

| 5,315,099 | A | * | 5/1994 | Gunz et al. .............. 250/201.1 |
| 5,377,032 | A | | 12/1994 | Fergason et al. |
| 5,751,258 | A | | 5/1998 | Fergason et al. |
| 5,940,150 | A | * | 8/1999 | Faris et al. ................... 349/16 |
| 6,483,090 | B1 | * | 11/2002 | Bae .......................... 250/201.1 |
| 6,501,443 | B1 | * | 12/2002 | McMahon .................... 345/52 |

OTHER PUBLICATIONS

WO 97 3431, Filter For Preventing Leakage of Electromagnetic Wave, Publication Date: Sep. 18, 1997.
WO 98 14040, A Protective Device For Shielding an Electrical Apparatus Against Environmental Conditions, Publication Date: Apr. 2, 1998.

* cited by examiner

Primary Examiner—Huy Mai
(74) Attorney, Agent, or Firm—Rankin, Hill, Porter & Clark LLP

(57) ABSTRACT

A glare-protection device contains an active filtering element (11) with influenceable light transmission such as a liquid crystal cell. The glare-protection device also contains an electronic circuit (3) for evaluating the output signal of a light sensor (5) and for driving of the filtering element (11), which electronic circuit (3) is attached to the internal surface (22) of a printed circuit board (2). The electronic circuit (3) has an evaluation circuit (31) and a driving circuit (32). A screening element (4), which is made out of electrically conductive material, is provided to screen at least a part of the evaluation circuit (31) against electro-magnetic radiation originating from the driving circuit (32), and is affixed to the same internal surface (22). Thanks to the screening element (4), the evaluation circuit (31) can be designed to be exceedingly sensitive, without it being excessively interfered with by electromagnetic influences. The screening element (4) keeps both interfering electro-magnetic influences, which emanate from the surroundings (91) of the glare-protection device as well as other influences that are produced in the glare-protection device itself, away from the evaluation circuit (31).

12 Claims, 3 Drawing Sheets

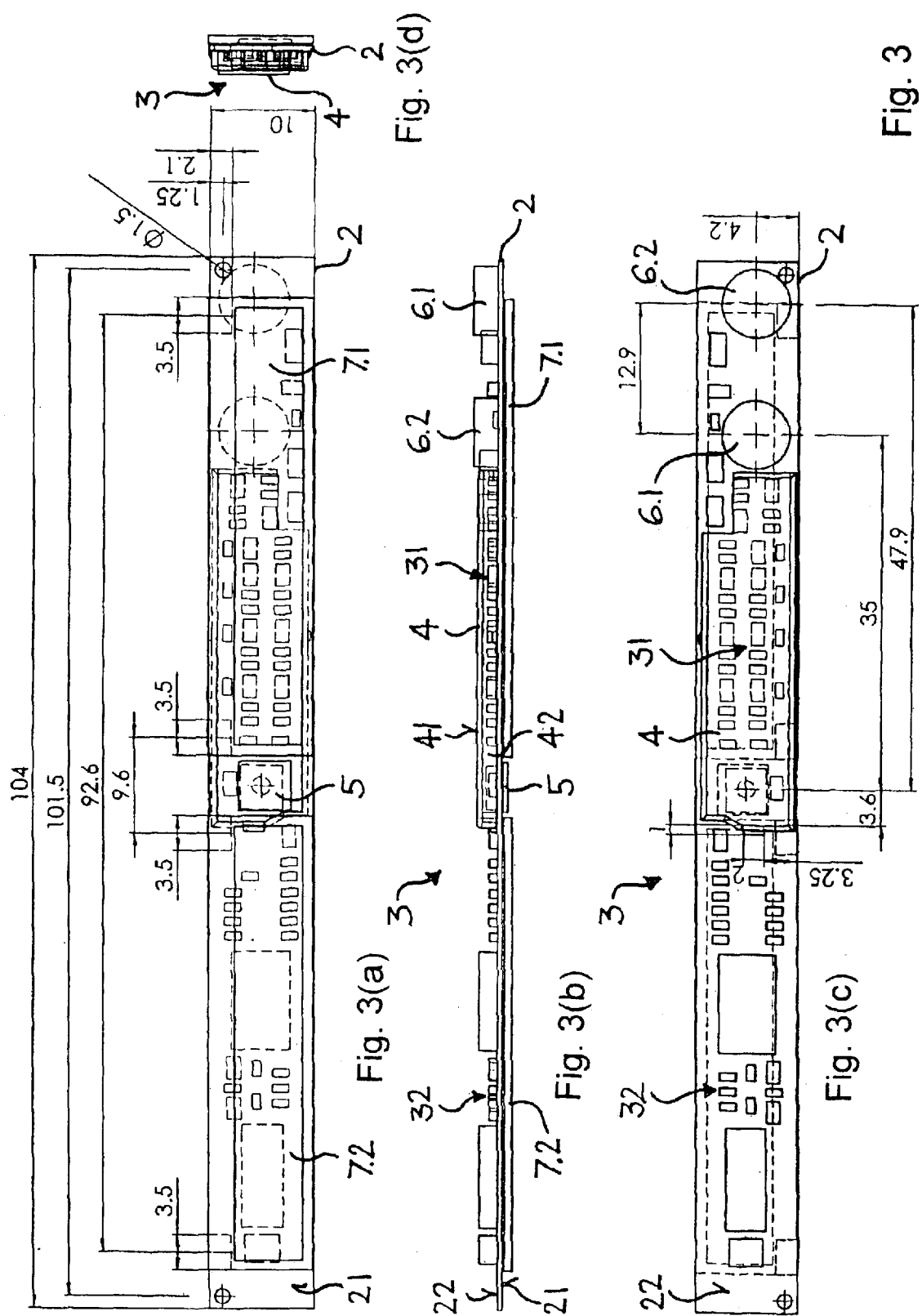

GLARE-PROTECTION DEVICE WITH A SCREENED EVALUATION CIRCUIT

BACKGROUND OF THE INVENTION

Field of the Invention

The invention is in the field of glare-protection devices, which, for example, are utilized as viewing windows for protection masks, helmets or goggles for welders. The invention is also related to the field of electro-magnetic compatibility (EMC) and concerns an EMC screening element for use in a glare-protection device.

Modern glare-protection devices, which are utilized, for example, as viewing windows for protection masks,—helmets and—goggles for welders, as active filtering elements typically contain at least one liquid crystal (LC) cell, which blocks the light transmission to a greater or lesser extent, as soon as the external light intensity exceeds a predefined threshold. For the detection of the light intensity a light sensor is utilized. An electronic circuit in the glare-protection device comprises an evaluation circuit for the sensor signal and a driving circuit for the liquid crystal cell.

The light sensor and the evaluation circuit detect so-called flickering light in the welding arc. Since modern welding processes operate with very low current values, the signal to be detected has an extremely low signal to noise ratio. For this reason it is difficult to differentiate between the flickering light content and other light contents and to extract the signal to be detected from the sensor output. In order for the evaluation circuit to be capable of doing this, it has to be designed to be very sensitive, i.e., with a high amplification. Such sensitive evaluation circuits, however, have the disadvantage that they are also sensitive to electro-magnetic interference signals. Interfering electro-magnetic influences can, for example, be produced by radiation from electric motors, from power inverters (e.g., of welding installations), from mobile telephones, etc.

Efforts up until now to find a solution to this problem, on the one hand, applied themselves to the evaluation circuit itself. It was attempted to design the evaluation circuit such that it picks up as few interfering signals as possible, and wherein, for example, critical conductor tracks are designed to be as short as possible.

On the other hand, one has recognized that the evaluation circuit also should be screened towards the outside against electro-magnetic interference. In doing so, one up to now concentrated on the outside or front side of the glare-protection device. In this regard, the outside or front side of the glare protection device is the side that is facing away from the carrier person and facing in the direction from which electro-magnetic interference signals are primarily expected. A common measure against such interference signals consists in equipping with electronic components only that side of the circuit board, which is facing inwards and to leave the surface facing outwards free of any components; simultaneously the external surface of the circuit board without any components is equipped with electro-magnetic screening means. Such screening means typically are a fine-mesh screen made of metallic conductor tracks. While these measures do produce some improvements, it has, however, become clear that the EMC screening achieved in this manner is still unsatisfactory for particularly sensitive circuits.

SUMMARY OF THE INVENTION

It is an objective of the invention to screen the evaluation circuit or parts of it from interfering electro-magnetic influences or interfering radiation in a better way than by the measures common up until now.

In accordance with the invention, electro-magnetic screening of the electronic components of the evaluation circuit takes place not only on the side of the printed circuit board without any components (i.e., from outside), but also on the side of the circuit board containing components (i.e., from inside). Foreseen therefore is an additional "protection behind the front". This measure in accordance with the invention leads to essential improvements in comparison with the up to the present moment usual protection "at the front".

The glare-protection device in accordance with the invention contains an active filtering element with a light transmission from an external half-space into an internal half-space, which can be influenced, and electronic components for the influencing of the filtering element, which are attached to at least one surface of a circuit board. The glare-protection device furthermore comprises a screening element containing electrically conductive material for the screening of electronic components against electro-magnetic radiation, which screening element is affixed to the at least one surface of the printed circuit board.

The screening elements in accordance with the invention for utilization in the glare-protection device contain electrically conductive material and has a concave shape.

The invention makes it possible to design the evaluation circuit to be exceedingly sensitive, without it being excessively subjected to interference by electro-magnetic influences. Interfering electro-magnetic influences on the one hand, as described above, emanate from the surroundings of the glare-protection device and are referred to hereinafter as external interaction. On the other hand, it has become manifest, that interfering electro-magnetic influences can also be produced within the glare-protection device itself, for instance in the driving circuit for the LC -cell. This is because glare-protection devices of today utilize digital modules, which generate interfering electro-magnetic radiation and also emit these to their surroundings. Also the LC cell itself can exercise undesirable electro-magnetic influences on the evaluation circuit. This "internal interaction" is particularly a problem when the glare-protection device has to be implemented in a small space. The concept in accordance with the invention (i.e., protection behind the front) makes possible a protection also against the internal interaction. This at first unexpected advantage is obviously jointly responsible for the exceptional effectiveness of the invention.

In many instances, the invention even makes possible a simplification of the evaluation circuit, because thanks to the EMC—screening one can make do without certain electronic filter elements. A further benefit of the invention consists in the fact that the screening protects the circuit not only against electro-magnetic radiation, but also against other detrimental physical and/or chemical influences, for example, against perspiration vapors from the carrier person.

BRIEF DESCRIPTION OF THE DRAWINGS

These and further features of the invention will be apparent with reference to the following description and drawings, wherein:

FIG. 3 is an evaluation circuit screened in accordance with the invention, where:

FIG. 3(a) is a front view of the evaluation circuit;

FIG. 3(b) is a top view of the evaluation circuit;

FIG. 3(c) is a rear view of the evaluation circuit; and

FIG. 3(d) is an end view of the evaluation circuit.

DETAILED DESCRIPTION OF THE PREFERRED EMBODIMENTS

Figure 1:
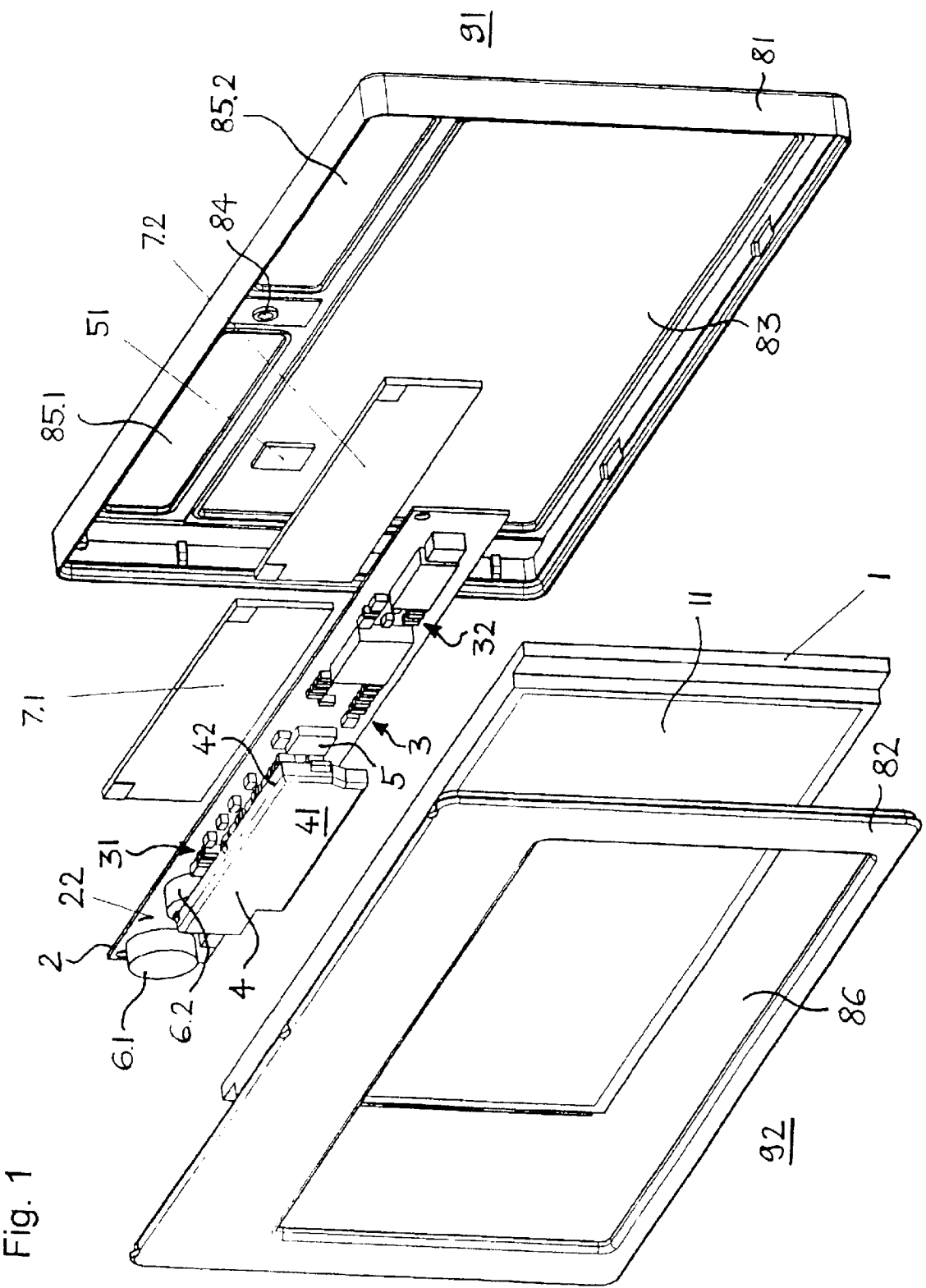
FIG. 1 is an exploded view of a glare-protection device with an evaluation circuit screened in accordance with the invention.
Figure 2:
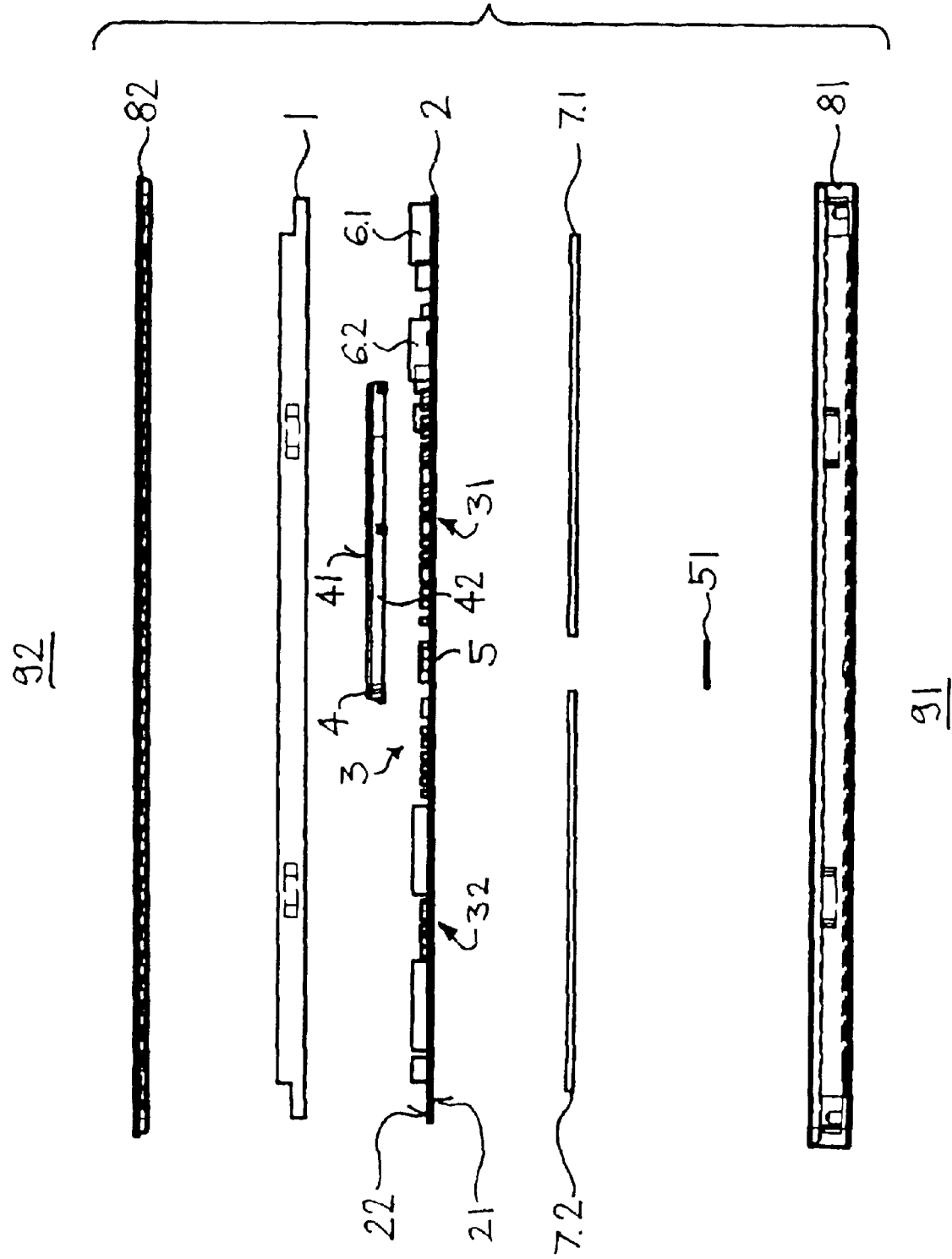
FIG. 2 is a plan view of the glare-protection device of FIG. 1.

FIGS. 1 and 2 in an exploded view drawing and a plan view, respectively, show an exemplary embodiment of a glare-protection device in accordance with the invention. FIG. 3 illustrates the electronic circuit with an evaluation circuit of the glare-protection device in accordance with the invention of FIGS. 1 and 2 screened in accordance with the invention; in it, (a) depicts a view from the outside, (b) a view from above, (c) a view from inside and (d) a view from the side. In FIG. 3, exemplary dimensions of the components are indicated in millimeters. In the following, this exemplary embodiment is explained making reference to the three drawing figures, whereby the same reference marks designate the same components.

The glare-protection device as its core component comprises an optical module 1 with an active filtering element 11, typically containing at least one liquid crystal cell, which blocks to a greater or lesser extent the light transmission from an external half-space 91 into an internal half-space 92 through the optical module 1. The glare-protection device further contains a printed circuit board 2. An external surface 21 of the printed circuit board 2 is equipped with screening means (not shown), for example, a fine-mesh screen made of metallic conductor tracks, for the purpose of screening against electro-magnetic radiation from the outside. On an internal surface 22 of the printed circuit board, an electronic circuit 3 is affixed. The electronic circuit 3 can, for example, comprise two part circuits 31, 32, an evaluation circuit 31 and a driving circuit 32. Attached to the printed circuit board is also a light sensor 5 for the detection of the external light intensity, which can be covered with a covering plate 51. The evaluation circuit 31 serves for the evaluation of the sensor output signal, the driving circuit 32 for driving the liquid crystal cell 11 in dependence of the sensor output signal. On the printed circuit board 2, electric energy storage devices 6.1, 6.2, such as batteries, can be installed. For the power supply, i.e., for the charging of the batteries 6.1, 6.2, on the front side of the glare-protection device photo-electric cells, solar cells 7.1, 7.2 can be provided. Belonging to the glare-protection device is in preference a cassette consisting of a cassette external part 81 and a cassette internal part 82, for example, made of plastic material. The cassette external part 81 is equipped with apertures 83, 84, 85.1, 85.2 for viewing, for the light sensor 5, and for the solar cells 7.1, 7.2. The cassette internal part 82 has an aperture 86 for viewing.

Above the evaluation circuit 31, on the internal surface 22 of the printed circuit board 2, a screening element 4 in accordance with the invention is attached. The screening element 4 is shaped such that it covers the evaluation circuit 31, or at least parts or components of it. In preference, it has a concave shape in the manner of a hood, so that it can cover electric and/or electronic components such as conductor tracks, contacts, resistances, capacitors, inductances, transistors, integrated circuits, etc. In the example of an embodiment illustrated here, the screening element 4 comprises an essentially rectangular plate 41 with a surface area of approx. 35×9 mm² and a thickness of approx. 0.5 mm. as well as at least partially protruding edges 42 of approx. 1.5 mm height, which are arranged along the circumference of the plate 41. These edges 42 are attached on the internal surface 22 of the printed circuit board 2 and materially positively connected with it in preference irreversibly, for example by means of soldering, gluing, spot welding, ultra-sound welding, mechanical friction, etc. However, also non-positive or frictional connections are possible. With these, the screening element 4 can be reversibly attached to the printed circuit board 2, removed as and when so required and possibly re-attached at another point.

The screening element 4 must contain electrically conductive material in order to, in the manner of a Faraday's cage, keep electro-magnetic interfering influences away from the evaluation circuit 31. It can, for example, consist of metal, a plastic material metallized on one surface, plastic material packed with metal particles, flexprint (i.e., a plastic foil, onto which electric conductor tracks are affixed), etc. Screening elements 4 made of metal can, for example, be made out of copper, brass, galvanized sheet metal, p-metal (i.e., a ferro-magnetic foil, e.g., made out of $Fe_{40}Ni_{40}B_{20}$ (atom %)) or of mixtures of these. Mentioned here as exemplary materials for the screening elements made out of plastic materials shall be PVC or Stat-Kon® RC-1006 (manufacturing company: LNP Engineering Plastics Inc., Exton, Pa.). Suitable as materials for the metallization of plastic for screening elements 4 are, for example, aluminum, copper, tin or mixtures of these. The screening element 4 can be manufactured as a foil, an injection molded part, molded part or a punched out—and bent to shape part.

In a preferred embodiment, the screening element 4 is electrically connected with electrically conductive elements on the printed circuit board 2 and its electric potential set to their zero conductor (mass). In this manner, capacitive influences are also screened. For this purpose, the screening element 4 is connected with the printed circuit board 2, for example, by soldering, gluing with a conductive adhesive, spot welding, ultrasound welding, mechanical friction, etc, In another embodiment, the electronic circuit 3 or parts of it could be attached to the outside of the printed circuit board 2 and screened with a screening element in accordance with the invention. Also belonging to the object of the invention are embodiments with several screening elements 4, which are attached either to a surface 21, 22 or both to the internal surface 22 as well as to the external surface 21 of the printed circuit board 2. The printed circuit board 2 can also be designed to be rigid or also flexible, i.e., as a foil printed circuit board; in case of a flexible printed circuit board 2, in preference a flexible screening element 4, for example made out of a foil, is utilized. With knowledge of the invention, the specialist can derive further embodiments from the examples indicated here.

What is claimed is:

1. A glare-protection device for utilization as a viewing window for protective masks for welders, comprising an active filtering element (11) with an influenceable light transmission from an external half-space (91) into an internal half-space (92), and an electronic circuit (3) for influencing the active filtering element (11), said electronic circuit having an evaluation circuit (31) and a driving circuit (32) that are installed on at least one surface (22) of a printed circuit board (2), wherein a screening element (4) is provided to screen at least a part of the evaluation circuit (31) against disturbing electro-magnetic influences, which originate from the driving circuit (32).

2. The glare-protection device according to claim 1, wherein the printed circuit board (2) has an internal surface (22) facing the internal half-space (92) and the electronic circuit (3) and the screening element (4) are attached to the internal surface (22) of the printed circuit board (2).

3. The glare-protection device according to claim 2, wherein the printed circuit board (2) has an external surface (21) facing the external half-space (91), said external surface being equipped with screening means against electromagnetic radiation, said screening means including a screen made of metallic conductor tracks.

4. The glare-protection device according to claim 1, further comprising a light sensor (5) for detection of a characteristic of light entering from the external half-space (91), and wherein the evaluation circuit (31) is operable to evaluate a sensor output signal.

5. The glare-protection device according to claim 1, wherein the screening element (4) has a concave shape.

6. The glare-protection device according to claim 1, wherein the screening element (4) comprises an essentially rectangular plate (41) and at least partially protruding edges (42), which are arranged along the circumference of the plate (41), and the edges (42) are attached to the printed circuit board (2).

7. The glare-protection device according to claim 1, wherein the screening element (4) is irreversibly connected with the printed circuit board (2) by means selected from the group consisting of soldering, gluing, spot welding, ultrasound welding and mechanical friction.

8. The glare-protection device according to claim 1, wherein the screening element (4) is electrically connected with electrically conductive elements on the printed circuit board (2).

9. The glare-protection device according to claim 1, wherein the screening element (4) contains metal, plastic material metallized on at least one surface, plastic material packed with metal particles and/or flexprint.

10. The glare-protection device according to claim 1, wherein the screening element (4) is manufactured as a foil, injection molded part, molded part or punched out and bent to shape part.

11. The glare-protection device according to claim 1, wherein the screening element (4) contains electrically conductive material.

12. The glare-protection device according to claim 1, wherein the screening element (4) comprises an essentially rectangular plate (41) and at least partially protruding edges (42), which are arranged along the circumference of the plate (41).

* * * * *